United States Patent [19]

Linkow

[11] Patent Number: 4,521,192
[45] Date of Patent: Jun. 4, 1985

[54] ORAL IMPLANT FOR OVERSIZED DENTAL SUPPORT OPENINGS

[76] Inventor: Leonard I. Linkow, 1530 Palisade Ave., Fort Lee, N.J. 07024

[21] Appl. No.: 516,184

[22] Filed: Jul. 21, 1983

Related U.S. Application Data

[63] Continuation-in-part of Ser. No. 418,244, Sep. 14, 1982, abandoned.

[51] Int. Cl.³ .............................................. A61C 8/00
[52] U.S. Cl. ..................................... 433/173; 433/176
[58] Field of Search ....................... 433/173, 175, 176; 3/1.91

[56] References Cited

U.S. PATENT DOCUMENTS

| | | | |
|---|---|---|---|
| 3,465,441 | 9/1969 | Linkow | 433/176 |
| 3,499,222 | 3/1970 | Linkow et al. | 433/174 |
| 3,683,501 | 8/1972 | Edelman | 433/176 |
| 3,729,825 | 5/1973 | Linkow et al. | 433/176 |
| 3,849,888 | 11/1974 | Linkow | 433/176 |
| 3,918,100 | 11/1975 | Shaw et al. | 3/1.91 |
| 3,925,892 | 12/1975 | Juillet | 433/176 |
| 4,081,908 | 4/1978 | Sneer | 433/176 |
| 4,180,910 | 1/1980 | Straumann et al. | 433/201 |
| 4,186,486 | 2/1980 | Gordon | 433/201 |
| 4,220,712 | 9/1980 | Staffolani | 433/173 |
| 4,302,188 | 11/1981 | Driskell | 433/176 |

FOREIGN PATENT DOCUMENTS

| | | | |
|---|---|---|---|
| 2237598 | 2/1974 | Fed. Rep. of Germany | 433/176 |
| 2628929 | 1/1977 | Fed. Rep. of Germany | 433/176 |
| 1228362 | 10/1960 | France | 433/173 |

*Primary Examiner*—John J. Wilson
*Attorney, Agent, or Firm*—Darby & Darby

[57] ABSTRACT

An oral implant allows for the immediate installation of an artificial tooth support structure in a jawbone portion which has become oversized due to a failed prior blade implant or an enlarged tooth socket. The implant includes one or more posts upon which the artificial tooth is mounted, as well as a support structure whose lateral dimensions is sufficient to permit it to be wedged in the oversized opening. Preferably, the lateral dimension is adjustable to various size openings in the jawbone.

26 Claims, 9 Drawing Figures

ORAL IMPLANT FOR OVERSIZED DENTAL SUPPORT OPENINGS

This is a continuation-in-part of application Ser. No. 418,244 filed Sept. 14, 1982, now abandoned.

BACKGROUND OF THE INVENTION

This invention relates to oral implants and, more particularly, to oral implants for use where tooth sockets or prior implant grooves have become oversized through previous failures or poor groove making technique by the oral surgeon.

Oral implants are used to mount artifical teeth where there is sufficient natural tooth structure for a conventional fixed bridge. These implants may be of the endosteal type, which include the pin and spiral screw implants disclosed in U.S. Pat. No. 3,499,222 which issued to the present inventor and his associates. These are inserted directly into the jawbone at the ridge crest. Other endosteal implants include the blade types described in U.S. Pat. No. 3,465,441, U.S. Pat. No. 3,729,825 and U.S. Pat. No. 3,849,888, all issued to the present inventor and his associates.

All of the endosteal implants include a blade or screw adapted to be seated in a tapped hole or groove, respectively, in the patient's jawbone. One or more posts extend from the blade or screw and are used to mount the artificial tooth or teeth. To locate the implant, an incision is made in the fibromucosal tissue at the ridge crest along the edentulous span involved. The tissue if then reflected to expose the jawbone. A groove is made in the jawbone if a blade is to be used or a hole is tapped and threaded in the bone if a screw type implant is used. The implant is then inserted in the jawbone opening and the tissue is sutured. After a period of time, the bone in the opening regrows and permanently fixes the implant in place.

On occasion, the implant fails because the blade or screw becomes loose before bone regeneration occurs. If a blade remains in place too long after it has become loose, it will enlarge the groove. A similar enlarged or oversized opening in the jawbone will be created when periodontally-involved teeth are over retained. When these teeth are finally removed, the sockets are extremely oversized.

Oversized openings in the jawbone prevent the immediate use of an implant. Typically a period of time is allowed to pass during which the bone regrows to fill the oversized opening and then a new and smaller opening for a new implant is created in the regenerated bone. However, this procedure necessarily leaves the patient without complete dentures for a considerable period of time.

SUMMARY OF THE INVENTION

The present invention is directed to an oral implant which can be used in oversized grooves or sockets in the jawbone without waiting for bone regrowth. This is accomplished by using an implant with a base or support that has a lateral dimension large enough to be wedged within the oversized opening. Preferably, the lateral dimension of the base or support is adjustable to permit it to be adapted for use in various size openings.

In an illustrative embodiment of the invention, the implant is in the form of a support adapted to be fitted horizontally in an oversized opening in the jawbone of a patient, which oversized opening is due to a previously failed implant blade or screw type implant or a group of over-retained periodontally involved teeth. The support has a lateral dimension that is sufficient to permit it to be wedged into the oversized opening. This lateral dimension may be due to two longitudinal helical structures which are joined to each other to form a double helix structure. Alternatively, the dimension can be due to a lateral sinuous shape, a basket shape, a cradle shape, a tubular shape or a pair of separated parallel blades. Regardless of the means by which the lateral dimension is created, one or more posts for supporting artificial teeth extend from the support structure.

In order to accommodate the various sizes of openings in the jawbone, the implant support may be constructed in a number of different sizes. Preferably, however, the lateral dimension of the implant support is made adjustable so that a single implant or group of implants can be made to fit in various size openings in the jawbone. This may be accomplished by making the support structure from a material which is relatively rigid, but which can be plastically deformed manually by the dentist or oral surgeon so that it fits within the opening in the jawbone of the patient under treatment.

BRIEF DESCRIPTION OF THE DRAWINGS

The foregoing and other features of the present invention will be more readily apparent from the following detailed description and drawings of illustrative embodiments of the invention in which.

DESCRIPTION OF EXEMPLARY EMBODIMENTS

Figure 1:
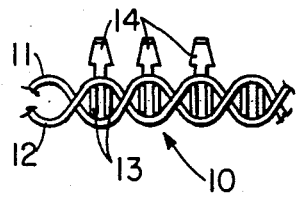
FIG. 1 schematically illustrates an oral implant with a fixed double helical support.

In FIG. 1 there is shown an implant designed with the same double helical structure as the microstructure of a DNA molecule. This implant is to be used in those areas where, due to a previously-failed implant blade or a group of over-retained periodontally-involved teeth, oversized grooves or sockets are left in the jawbone. In particular, the implants of this type are designed for immediate reentry procedures into a destroyed groove, i.e. entry prior to bone regeneration into a groove that is much wider bucco-lingually than the original groove that is typically made with a number 700 XL bur. This implant includes a support 10 which is in the form of two longitudinal helical coil structures 11, 12 which are permanently joined by cross members 13. Projecting from the upper portion of the support structure 10 are three posts 14 which are adapted for mounting artificial teeth in a conventional manner. However, it can also be made with one or two such posts. Further, the center post in a normal group of three posts for three artificial teeth can be eliminated with the two end posts being used to support a bridge mounting the center tooth.

To install the implant, all of the granulation tissue is removed from the groove. There is no need to create a new groove with the number 700 bur at the base or floor of the old groove. Then the implant is wedged horizontally into the oversized groove such that posts 14 are in line with the remaining teeth along the patient's jawbone and the lateral edges of the implant wedge or compress the surrounding alveolar walls of the groove. Bone fragments, taken from the symphysis or iliac crest, sterile Plaster of Paris mixed with sterile saline, or Calcitite (hydroxylappatite) or Synthograft (tri-calcium-phosphate resorbable material) mixed with patient's blood can be placed in the area of the groove that remains after the implant is wedged into position. Alternatively, the patient's blood can merely be allowed to clot around the implant. New bone will eventually grow so as to totally fill the area about the support of the implant, provided it does not loosen from the first day of insertion.

In order to accommodate various sizes of grooves, different size support structures 10 may be provided or the cross members 13 may be of plastically-deformable material so that the oral surgeon can change the configuration of support 10 until it has a lateral dimension which permits it to be tightly fitted against the remaining alveolar walls of the groove. This material can be a thin sheet of metal which is relatively inert in the oval cavity, e.g. stainless steel or titanium.

Figure 2:
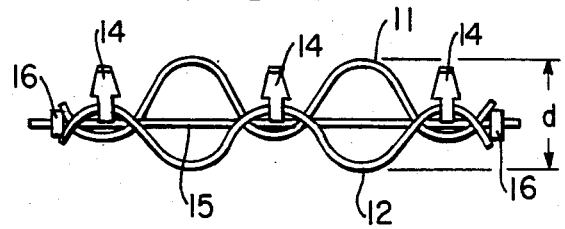
FIG. 2 illustrates an oral implant with an adjustable helical support.

FIG. 2 illustrates a double helical support for an oral implant which is similar to that shown in FIG. 1. However, in this case, the two helical sections 11, 12 are pivotally joined by a connecting rod 15. This rod connects the helical sections at locations offset from their center so that rotation of one section with respect to the other will increase or decrease the lateral dimension d of the support until it has a size that will allow it to be tightly fitted in the groove. Once the correct size has been obtained, bolts 16 on the threaded ends of rod 15 are tightened to hold it in place.

With this arrangement, the posts 14 extend from rod 15 so that it can be guaranteed that they have a vertical direction regardless of the setting of the helical sections 11, 12.

Figure 3:
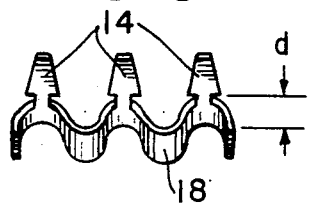
FIG. 3 illustrates an oral implant with a coiled or sinuous support structure.
Figure 9:
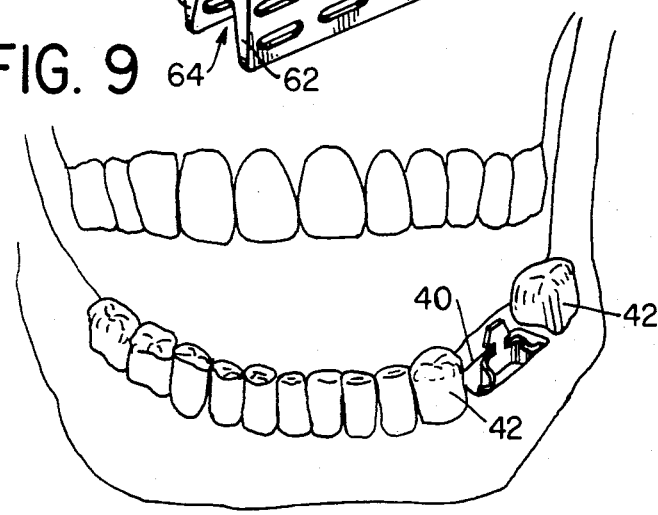
FIG. 9 is a schematic illustration of a portion of mandible with the implant of FIG. 3 inserted in an oversized opening therein.

FIG. 3 illustrates an oral implant with a laterally sinuous or coiled shape for its support structure 10. In general, the support is a strip 18 with a rectangular cross section which has been laterally bent into the coil shape. The implant as shown has three posts 14 for mounting artificial teeth, but it can also be made with one or two such posts or it can be cut shorter so as to eliminate one post. These posts 14 extend from the upper or superior surface of the support and act for mounting artificial teeth when the implant is inserted in a groove 40 positioned between healthy teeth 42 as shown in FIG. 9. Also, this implant can be used totally as a posterior abutment or it can be used as the sole abutment in totally endentulous jaws (upper and lower). As with the double helical support structures of FIGS. 1 and 2, the lateral coiled strip structure can be designed in several different sizes to accommodate different size openings in the jawbone or it can be made of material which is manually, plastically deformable by the oral surgeon so that its lateral dimension d can be changed to accommodate different size grooves in the jawbone.

Figure 4:
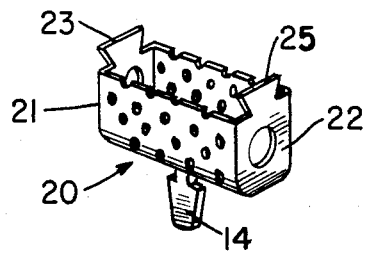
FIG. 4 illustrates an oral implant with a perforated basket support structure.

An endo-sub-ridge augmenting implant is shown in FIG. 4. This implant has a perforated basket support 20 with a generally U-shaped cross section that is open at the upper end. While the implants shown in FIGS. 1-3 were shown with the posts 14 projecting upward, which would be the suitable insertion position for locating them in a groove in the lower jawbone or mandible, the implant of FIG. 4 is shown with the post projecting downward, such as would be the case if it were inserted in a groove in the maxillary arch.

The ends of the basket 20 are closed by end walls 21, 22 which are also perforated. These end walls are located at both the mesial and distal extremes of the implant and support blade-like extensions 23 and 25. By virtue of the bucco-lingual blade-like extensions, the implant can be held steady in position when these blade portions are tapped into corresponding grooves made in the bone at positions distal and mesial to both corresponding extensions of the maxillary sinus.

The large horizontal perforated basket 20 of the implant not only acts to fill oversized grooves, it can be filled with bone from the patient's iliac crest or symphysis or with synthetic bone, such as Calcitite (hydroxylappatite), Synthograft (tri-calcium phosphate), etc., and used to augment the bone in the maxillary ridge. The amount by which the basket is allowed to extend over the residual crest after the bucco-lingual blade portions are tapped into the bone, will determine how high the redge augmentation will be. If the residual ridge crest is too wide bucco-palatally for the basket to fit over it, a few vertical cuts with a scissor or similar shearing instrument along the peripheral edges of the basket is all that is necessary to allow the basket to be spread out so as to straddle the wider ridge.

Figure 5:
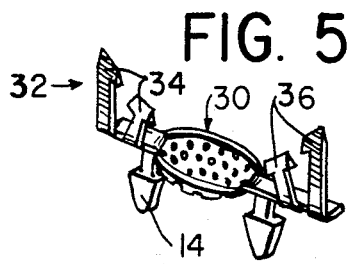
FIGS. 5 and 6 illustrate oral implants with cradle-shaped support structures.
Figure 6:
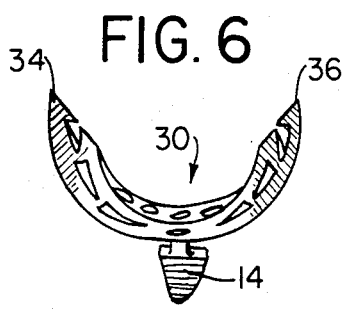

In FIGS. 5 and 6 an implant structure similar to that in FIG. 4 is shown, except that the basket has been replaced with a cradle structure 30. This cradle is adapted to carry bone fragments, as does the basket in FIG. 4, and is supported by a blade body or auxiliary support structure 32 in a mesial distal direction. The shape of the auxiliary support or blade body structure of FIG. 5 creates blades 34, 36 at its ends. In the embodiment of FIG. 6, the blades 34, 36 are made at the ends of the cradle. For both cases, the shape of the implant support is made to follow the many variable configurations of the sinus floors where the implant is to be used. The post 14 for mounting an artifical tooth extends from the basket 30. In this arrangement, either the blade body 32 or the entire cradle is perforated. These perforations, as with the perforations in the embodiment of FIG. 4, are included because they promote bone regeneration and more rigidly secure the implant when new bone grows through these openings. Also, in order to allow the cradle to fit in grooves of various sizes, it can be made of plastically-deformable material.

In addition to being used as an implant for oversized grooves, the device of FIGS. 5 and 6 can also be used as a sinus lift bone donor. In particular, it can be used for lifting the soft maxillary sinus floor, i.e. the Schneiderian membrane, and the bone fragments included within the hammock-like cradle can be placed beneath this floor to thicken the bone there. By raising the Schneiderian membrane, the sinus is actually shrunk in size. The higher up the floor is pushed and the more bone that is placed inside the cradle, the smaller the sinus cavity will become and the higher and thicker the underlying, newly-formed alveolar crest will become. The cradle is porous or has tiny vents throughout its entire surface for better healing of the mucoperiosteal tissue.

The technique for using the implant as a sinus lift bone donor involves making an incision through the mucoperiosteal tissues to expose the underlying bone mesial and distal to the near sinus exposure. If the membrane is not exposed because a small amount of bone is present, this bone is carefully removed with a large round bur to expose the same mesial-distal or near mesial-distal length of the membrane as the mesial-distal length of the particular cradle size of the implant of choice. Then a number 700 bur is used to make the normal blade grooves in the good bone that exists mesially and distally to the Schneiderian membrane and blades 34, 36 are gently tapped into the grooves. The bone fragments within the cradle and the cradle itself push up the sinus floor and add new bone in that area. The tissues are then sutured closed.

The advantage of this particular implant is that it allows support for a fixed prosthesis where no other implant type could be used. Also, it allows a build-up of the ridge with new bone formation beneath the raised sinus floor and underneath the periosteum and muscosal tissues.

Figure 7:
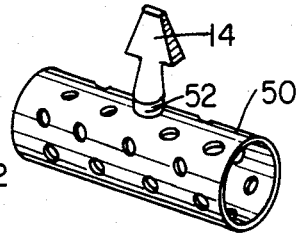
FIG. 7 illstrates an oral implant with a porous tubular support structure.

A further implant with a hollow porous tubular support 50 is shown in FIG. 7. The support structure 50 may have one or more posts 14 mounted thereto, e.g. by way of screw threads 52. Like the other implants previously described, this implant can be inserted into a groove that was widened due to the failure of a previous blade and this insertion can be made immediately after the removal of the failed blade without waiting for bone regrowth. Also, bone fragments, either natural or synthetic, can be placed inside the tube to promote more rapid healing. Preferably, the support is also plastically deformable. If desired, the tubular portion can be buried in the jaw for several months before the post is screwed in place. As a result, the tubular support will have time to be firmly fixed in place before the stresses from the post and artificial tooth are applied to it.

Figure 8:
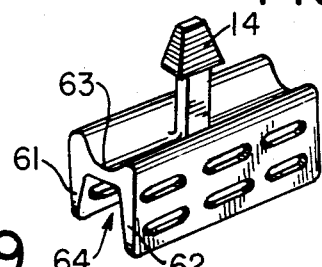
FIG. 8 illustrates an oral implant with a dual blade support structure.

The implant of FIG. 8 is formed with a support that has two blade bodies 61, 62 that are connected together by a flange 63 that supports a post 14. Typically, the implant is made so that the blades can be spread out or tapered inwardly to accommodate an excessively wide groove in the jaw due to a previously-failed blade. A space 64 between the blades can be filled with bone, either natural or synthetic, to promote the rapid retention of the implant. Like the other implants described herein, this bi-blade or dual blade implant can be used in an immediate re-entry procedure as soon as the failed blade has been removed. Most of the time the oral surgeon need not make another groove in the jaw. Instead, the blade is merely wedged against the walls surrounding the area of the failed blade. Sometimes a groove is preferably made at the buccal inferior line angle and at the inferior lingual line of the oversized groove and the bi-blade is tapped into position.

While the invention has been particularly shown and described with reference to preferred embodiments thereof, it will be understood by those skilled in the art that various changes in form and details may be made therein without departing from spirit and scope of the invention.

What is claimed is:

1. An oral implant for permanently implanting an artificial tooth supporting structure in at least one opening in an alveolar ridge crest of a patient in which a support for a natural or artificial tooth was previously located, said opening having an upper rim and being oversized with respect to that in which a tooth support is normally positioned, comprising:

an integral support adapted to be fitted horizontally in the oversized opening, said support having a lateral dimension that is adjustable by plastic deformation sufficient to permit the support to be wedged tightly against the alveolar walls of the opening, said lateral dimension being defined by two parallel lateral side portions of the support adapted to contact the alveolar walls in generally parallel planes below the upper rim of the opening; and at least one post extending from the support in a direction opposite the oversized opening when the implant is installed, said post being adapted for the mounting of an artificial tooth.

2. An oral implant as claimed in claim 1 wherein the support includes a blade structure extending in the direction towards the oversized opening when the implant is installed, said blade being adapted for being driven into the jawbone at the floor of the oversized opening.

3. An oral implant as claimed in claim 1 wherein the support is formed from a pair of generally parallel blades connected together by a flange at a distance from each other.

4. An oral implant as claimed in claim 3 wherein the blades are perforated.

5. An oral implant as claimed in claim 3 wherein the spacing between the blades, at least at their ends, is plastically and manually adjustable.

6. An oral implant for permanently implanting an artifical tooth supporting structure having at least one opening in an alveolar ridge crest of a patient in which a support for a natural or artifical tooth was previously located, said opening being oversized with respect to that in which a tooth support is normally positioned, comprising, a support in the form of two longitudinal helical structures fastened to each other by cross members, said support being adapted to be fitted horizontally in the oversized opening and having a lateral dimension that is sufficient to permit the support to be wedged tightly against the alveolar walls of the opening; and at least one post extending from the support in the direction opposite the oversized opening when the implant is installed, said post being adapted for the mounting of an artificial tooth.

7. An oral implant as claimed in claim 6 wherein the lateral dimension of the support is adjustable in size by manually bending said cross members.

8. An oral implant as claimed in claim 6 wherein the cross members are made of a plastically-deformable material so the helical structures can be moved with respect to each other to change the lateral dimension of the support.

9. An oral implant as claimed in claim 6 wherein bone fragments are located within the helical structures when the implant is inserted in the jawbone.

10. An oral implant for permanently implanting an artificial tooth supporting structure in at least one opening in an alveolar ridge crest of a patient in which a support for a natural or artificial tooth was previously located, said opening being oversized with respect to that in which a tooth support is normally positioned, comprising:

a support in the form of two longitudinal helical structures adapted to be fitted horizontally in the oversized opening;

means for pivotally and eccentrically connecting the helical structures with respect to each other so that rotational movement of one with respect to the other changes the lateral dimension of the support sufficiently to permit the support to be wedged tightly against the alveolar walls of the opening;

means for fixing said helical structures in selected pivotal positions with respect to each other; and at least one post extending from the means for connecting the helical structures in a direction opposite the oversized opening when the implant is installed, said post being adapted for the mounting of an artificial tooth.

11. An oral implant as claimed in claim 10 wherein bone fragments are located within the helical structure when the implant is inserted in the jawbone.

12. An oral implant for permanently implanting an artificial tooth supporting structure in at least one opening in an alveolar ridge crest of a patient in which a support for a natural or artificial tooth was previously located, said opening being oversized with respect to that in which a tooth support is normally positioned, comprising:

a support in the form a longitudinal strip with a lateral sinuous shape in a plane generally parallel to an occusal plane of the patient, said strip being adapted to be fitted horizontally in the oversized opening, the lateral sinuous excursions being sufficient to meet the respective lateral alveolar walls of the opening that extend generally parallel to the occusal plane of the patient such that the support can be wedged tightly against the alveolar walls of the opening, said strip being made of a plastically deformable material such that the lateral dimension of the support is adjustable; and at least one post extending from the support in the direction opposite the oversized opening when the implant is installed, said post being adapted for the mounting of an artificial tooth.

13. An oral implant for permanently implanting an artificial tooth supporting structure in at least one opening in an alveolar ridge crest of the patient in which a support for a natural or artificial tooth was previously located, said opening being oversized with respect to that in which a tooth support is normally positioned, comprising:

a support in the form of a longitudinal perforated basket with a generally U-shaped cross section, said basket being adapted to be fitted horizontally in the oversized opening and having two perforated end walls at the mesial and distal extremes, respectively, said basket having an open side directed towards the oversized opening;

at least one post extending from the part of the basket opposite the open side when the implant is installed, said post being adapted for the mounting of an artificial tooth; and said basket having peripheral edges adapted to be cut and spread, said basket also being made of a plastically-deformable material so that the edges can be permanently deformed to adjust its lateral dimension sufficiently to permit the support to be wedged tightly against the alveolar walls of the opening.

14. An oral implant for permanently implanting an artificial tooth supporting structure in at least one opening in the alveolar ridge crest of a patient in which a support for a natural or artificial tooth was previously located, said opening being oversized with respect to that in which a tooth support is normally positioned, comprising:

a support in the form of a longitudinal cradle with an open part directed into the oversized opening, said cradle being made of a plastically-deformable material so that it can be permanently deformed to adjust its lateral dimension sufficiently to permit the support to be wedged tightly against the alveolar walls of the opening; and at least one post extending from the part of the cradle opposite the open end, said post being adapted for the mounting of an artificial tooth.

15. An oral implant for permanently implanting an artificial tooth supporting structure in at least one opening in an alveolar ridge crest of a patient in which a support for a natural or artificial tooth was previously located, said opening being oversized with respect to that in which a tooth support is normally positioned, comprising:

a support in the form of a longitudinal strip with a lateral sinuous shape in a plane generally parallel to an occlusal plane of the patient, said strip being adapted to be fitted horizontally in the oversized opening, the lateral sinuous excursions being sufficient to meet the respective lateral alveolar walls of the opening that extend generally parallel to the occlusal plane of the patient such that the support can be wedged tightly against the alveolar walls of the opening; and at least one post extending from the support in a direction generally perpendicular to the plane of the lateral sinuous shape and extending from the support in the direction opposite the oversized opening when the implant is installed, said post being adapted for the mounting of the artificial tooth.

16. An oral implant as claimed in claim 15 wherein the strip has a generally rectangular cross section with the post extending from one narrow side of the rectangle and a blade portion extending from the other narrow side when the implant is installed.

17. An oral implant for permanently implanting an artificial tooth supporting structure in at least one opening in alveolar ridge crest of a patient in which a support for a natural or artificial tooth was previously located, said opening being oversized with respect to that in which a tooth support is normally positioned, comprising:

a support in the form a longitudinal perforated basket with a generally U-shaped cross section, said basket having two perforated end walls at the mesial and distal extremes, respectively, said basket also having an open side directed towards the oversized opening; and at least one post extending from the part of the basket opposite the open side, said post being adapted for the mounting of the artificial tooth.

18. An oral implant as claimed in claim 17 wherein the support comprises blades at the respective end walls.

19. An oral implant as claimed in claim 17 wherein the basket is filled with bone fragments when the implant is inserted into the jawbone.

20. An oral implant for permanently implanting an artificial tooth supporting structure in at least one opening in the alveolar ridge crest of a patient in which a support for a natural or artificial tooth was previously located, said opening being oversized with respect to that in which a tooth support is normally positioned, comprising:

a support in the form of a longitudinal cradle with an open part directed into the oversized opening when installed, said cradle having a generally arcuate longitudinal cross section and a generally arcuate transverse cross section so as to form a container with closed ends; and at least one post extending from the part of the cradle opposite the opened part, said post being adapted for the mounting of an artificial tooth.

21. An oral implant as claimed in claim 20 wherein the cradle is attached to a perforated auxiliary support extending to either end, said auxiliary support includes blades.

22. An oral implant as claimed in claim 20 wherein said cradle is perforated and its ends include blades.

23. An oral implant as claimed in claim 20 wherein said cradle contains bone fragments when the implant is installed in the jawbone.

24. An oral implant for permanently implanting an artificial tooth supporting structure in at least one opening in the alveolar ridge crest of a patient in which a support for a natural or artificial tooth was previously located, said opening being oversized with respect to that in which a tooth support is normally positioned, comprising:

a support in the form of a longitudinal cylindrical hollow tube formed by a circumferential side wall, said hollow tube being adapted to be located longitudinally in the opening; and at least one post extending from the circumferential side wall of the tube generally perpendicular to the longitudinal axis of the tube, said post being adapted for the mounting of an artificial tooth.

25. An oral implant as claimed in claim 24 wherein the hollow tube is perforated.

26. An oral implant as claimed in claim 24 wherein said at least one post is threaded into the hollow tube so as to extend radially therefrom.

* * * * *